(12) United States Patent
Wolter (10) Patent No.: US 8,287,542 B2
(45) Date of Patent: Oct. 16, 2012

(54) REPOSITIONING AND FIXATION SYSTEM FOR BONE FRAGMENTS

(76) Inventor: Dietmar Wolter, Holsdorf (DE)

( * ) Notice: Subject to any disclaimer, the term of this patent is extended or adjusted under 35 U.S.C. 154(b) by 458 days.

(21) Appl. No.: 12/520,813

(22) PCT Filed: Dec. 12, 2007

(86) PCT No.: PCT/EP2007/010898
§ 371 (c)(1),
(2), (4) Date: Mar. 4, 2010

(87) PCT Pub. No.: WO2008/077493
PCT Pub. Date: Jul. 3, 2008

(65) Prior Publication Data
US 2010/0179552 A1 Jul. 15, 2010

(30) Foreign Application Priority Data
Dec. 22, 2006 (DE) .......... 10 2006 062 164

(51) Int. Cl.
*A61B 17/80* (2006.01)
(52) U.S. Cl. .......... 606/71; 606/286
(58) Field of Classification Search .......... 606/606, 606/70, 71, 246–279, 280–299
See application file for complete search history.

(56) References Cited

U.S. PATENT DOCUMENTS

| | | | |
|---|---|---|---|
| 6,325,803 B1* | 12/2001 | Schumacher et al. | 606/71 |
| 6,336,927 B2* | 1/2002 | Rogozinski | 606/286 |
| 6,379,354 B1* | 4/2002 | Rogozinski | 606/260 |
| 7,090,676 B2* | 8/2006 | Huebner et al. | 606/71 |
| 7,628,816 B2* | 12/2009 | Magerl et al. | 623/17.16 |
| 7,695,473 B2* | 4/2010 | Ralph et al. | 606/71 |
| 2003/0055429 A1* | 3/2003 | Ip et al. | 606/69 |
| 2004/0102778 A1* | 5/2004 | Huebner et al. | 606/71 |

(Continued)

FOREIGN PATENT DOCUMENTS

DE 7517440 12/1976

(Continued)

OTHER PUBLICATIONS

International Search Report and Written Opinion mailed on Mar. 27, 2008 directed at application No. PCT/EP2007/010898; 20 pages.

*Primary Examiner* — Kevin T Truong
*Assistant Examiner* — Christopher Beccia
(74) *Attorney, Agent, or Firm* — Morrison & Foerster LLP (57) ABSTRACT

The repositioning and fixation system according to the invention comprises at least two bone plates that are designed to be interconnected. Each bone plate is provided with a connector element for connection to another bone plate. The connector element of a first bone plate comprises a plurality of projections. The connector element of a second bone plate comprises an opening. In a first connection state, the projections engage in the opening and produce a hinge-type connection between the first bone plate and the second bone plate. In a second connection state, the projections are tensioned and produce a rigid connection between the first bone plate and the second bone plate. With the repositioning and fixation system according to the invention, bone fragments secured to the bone plates can be repositioned by pivoting of the bone plates. Once the bone fragments have been brought to their final position, the projections can be tensioned in such a way that the bone plates are rigidly interconnected.

12 Claims, 6 Drawing Sheets

U.S. PATENT DOCUMENTS

| | | | |
|---|---|---|---|
| 2004/0127903 A1* | 7/2004 | Schlapfer et al. | 606/69 |
| 2004/0159757 A1 | 8/2004 | Pfister | |
| 2005/0021033 A1* | 1/2005 | Zeiler et al. | 606/70 |
| 2005/0085819 A1* | 4/2005 | Ellis et al. | 606/71 |

FOREIGN PATENT DOCUMENTS

| | | |
|---|---|---|
| DE | 4223794 | 1/1994 |
| DE | 4343117 | 6/1995 |
| DE | 19629011 | 1/1998 |
| DE | 19834326 | 2/2000 |
| DE | 19858889 | 6/2000 |
| DE | 102004035546 | 2/2006 |
| EP | 0628289 | 12/1994 |
| EP | 1211993 | 6/2002 |
| WO | WO-2004/045389 | 6/2004 |

\* cited by examiner

Fig. 14

REPOSITIONING AND FIXATION SYSTEM FOR BONE FRAGMENTS

REFERENCE TO RELATED APPLICATIONS

This application is a national stage application under 35 USC 371 of International Application No. PCT/EP2007/010898, filed Dec. 12, 2007, which claims the priority of German Patent Application No. 10 2006 062 164.6, filed Dec. 22, 2006, the contents of which prior applications are incorporated herein by reference.

FIELD OF THE INVENTION

The invention relates to a repositioning and fixation system with which bone fragments can be repositioned and then fixed.

BACKGROUND OF THE INVENTION

For over a century, bone fragments have been fixed relative to each other with the aid of bone plates, screws and nails. The fixation of bone fragments by means of traditional bone plates requires that the bone fragments are already repositioned, that is to say are in the correct position relative to each other. The traditional bone plate is placed onto the repositioned bone fragments and is secured to the bone fragments by screws or nails.

A repositioning and fixation system is also known which is made up of two bone plates that are interconnected like a hinge. The two bone plates are connected to different bone fragments. It is not necessary for the bone fragments to have already been reset in their final position when the bone plates are secured. Instead, the bone plates, with the bone fragments secured to them, can be pivoted relative to each other about the hinge axis in order to reposition the bone fragments. Such a repositioning and fixation system is provided for a distal fracture of the radius in the wrist area.

SUMMARY OF THE INVENTION

A disadvantage of the known repositioning and fixation system is that in many cases, when the bone fragments have been repositioned by pivoting of the bone plates, it can be difficult to fix the bone fragments in the final position. An object of the invention is to provide a repositioning and fixation system that makes it easier to fix the bone fragments after they have been repositioned.

The repositioning and fixation system according to the invention comprises at least two bone plates that are designed to be interconnected. If necessary, any desired number of bone plates can be connected to one another. Each bone plate is provided with a connector element for connection to another bone plate. The connector element of a first bone plate comprises a plurality of projections. The connector element of a second bone plate comprises an opening. In a first connection state, the projections engage in the opening and produce a hinge-type connection between the first bone plate and the second bone plate. In a second connection state, the projections are tensioned and produce a rigid connection between the first bone plate and the second bone plate.

In the context of the invention, a hinge-type connection of two bone plates is understood as meaning a connection that permits a pivoting of the bone plates about the hinge axis as the only movement. In a rigid connection, movement of the bone plates relative to each other is no longer possible.

With the repositioning and fixation system according to the invention, bone fragments secured to the bone plates can be repositioned by pivoting of the bone plates. Once the bone fragments have been brought into their final position, the projections can be tensioned such that the bone plates are rigidly interconnected. The bone fragments connected to the bone plates are in this way fixed in their final position.

In an advantageous embodiment, the first bone plate has a bore and the projections are arranged at the circumference of the bore. Such a bore affords the possibility of guiding a screw through the opening in the second bone plate and through the bore in the first bone plate and screwing it into an adjacent bone fragment. The tensile force that is generated by the screwing-in of the screw can at the same time be used to tension the projections in the second connection state. Preferably, the head of the screw engages on the projections and subjects the latter to tensioning. For this purpose, the head of the screw can have a conical outer shape.

The tensile force necessary for tensioning the projections can be generated by screwing the screw into a bone fragment. In many cases, however, the bone fragments are spongy and do not provide a sufficient hold for the thread of the screw. It may therefore be advantageous if the screw, even without a secure hold in a bone fragment, is in rigid connection to the first and second bone plates. It is possible that the opening in the second bone plate or the bore in the first bone plate has a thread that cooperates with the thread of the screw. With the aid of this thread, the projections can be tensioned independently of the holding force of the adjacent bone fragment, and in this way a rigid connection can be produced between the first bone plate, the second bone plate and the screw.

It has proven advantageous if the opening or the bore is not already provided with a thread from the outset and instead the thread is generated only as the screw is being screwed in. The thread of the screw and the wall of the opening or bore cooperate in such a way that the wall of the opening or of the bore is subject to cold-forming. To make it easier to screw the screw into place, the bone plate can have an area of reduced hardness in the region around the opening or bore (cf. DE 196 29 011 A1). For example, a screw head made of a harder titanium material can form its way into an area of the bone plate made of softer pure titanium. The screwing-in of the screw and the associated cold-forming can be made easier if the material thickness in this area is reduced. In particular, the wall of the opening or bore can have a constriction of smaller material thickness in the form of a burr, a lip or an edge (cf. EP 1 211 993 B1).

It is not absolutely necessary for the screw to be screwed in perpendicular to the bone plate or parallel to the bore. Instead, the screw can be screwed into the bone plate at various angle settings, a stable connection between the bone screw and the bone plate still being achieved at this angle setting (cf. DE 198 58 889 A1, DE 43 43 117 C2). Connections of this kind are also referred to as having multidirectional angle stability.

In the initial state, the first bone plate and the second bone plate are present as separate parts. To bring the first bone plate and second bone plate into the first connection state, the projections of the first bone plate are brought into engagement with the opening of the second bone plate. Two segments of the projections are differentiated below. The projections jut out from the plane of the first bone plate. A segment of a projection close to the bone plate adjoins the first bone plate, and the projection is connected to the first bone plate via the segment close to the bone plate. The segment of a projection remote from the bone plate faces away from the first bone plate and forms the free end of a projection. To permit an engagement of the projections in the openings, the projections can be designed in such a way that their segments remote from the bone plate can be connected to an imaginary circle in an untensioned state, and that the diameter of the circle is greater than the diameter of the opening in the second bone plate. When the opening is pushed onto the projections, the projections are tensioned inward, such that the diameter of the imaginary circle reduces and the opening can be pushed over the ends of the projections remote from the bone plate.

The segments of the projections close to the bone plate are preferably designed in such a way that, in an untensioned state, they can be connected to an imaginary circle whose diameter corresponds to the diameter of the opening of the second bone plate. When the second bone plate is pushed with the opening over the segments remote from the bone plate, the projections spring from their inwardly tensioned position back to the untensioned position. The segments of the projections close to the bone plate lie on the inner circumference of the opening. When the second bone plate is pivoted relative to the first bone plate, the inner wall of the opening rotates relative to the projections. The segments of the projections close to the bone plate form, together with the inner wall of the opening, the bearing of the hinge-type connection between the first bone plate and second bone plate.

The opening in the second bone plate, into which the projections engage, can be designed in such a way that it completely surrounds the projections in the first connection state. For this purpose, a bead can be formed on the inner wall of the opening, and the projections engage behind said bead.

The rigid connection that exists in the second connection state between the first bone plate and the second bone plate is produced by means of the projections being tensioned. The tensioning can involve the projections being spread apart. The spreading apart causes the outer faces of the projections to be pressed against the inner wall of the opening. The friction between the projections and the inner wall of the opening increases, such that the bearing of the hinge-type connection has considerably increased resistance. It is advantageous if the tensioning of the projections causes not only an outwardly directed spreading force, but also a force by which the second bone plate is pressed against the first bone plate. Such a combination of forces can be achieved, for example, by the projections being tilted. The combined force has the effect that the friction also increases in the contact area in which the first bone plate and the second bone plate lie flat on each other. The resistance-increasing effect of the friction in the contact area can be further strengthened if at least one of the bone plates has elevations and depressions in the contact area. The purpose of the friction is to make a pivoting movement between the first bone plate and the second bone plate difficult. The elevations and depressions offer the greatest resistance to a pivoting movement when they are oriented radially with respect to the bore in the first bone plate and/or to the opening in the second bone plate.

In a preferred embodiment, one or more bone plates have more than one connector element for connecting to other bone plates. This opens up the possibility of interconnecting a plurality of bone plates. Bone plates having an elongate shape have proven suitable for use in the repositioning and fixation system according to the invention. In addition to the connector elements, the bone plates can have other bores via which the bone plate can be connected to bone fragments. Normal screws can be used in these bores. However, it is also possible to use screws that connect to the bone plates in the process of cold-forming (cf. DE 198 58 889 A1, DE 43 43 117 C2). If individual bores are not needed for a screwed connection, these bores remain free and can be sealed with filler bodies in order to stabilize the bone plate. This is known from DE 10 2004 035 546 A1.

Following bone fractures, it is often difficult to bring the bone fragments back to the correct position relative to each other. The bone fragments may be greatly displaced by attached muscles. Soft tissue parts may become wedged between the bone fragments. Access to the fracture site may be made difficult by soft-tissue parts lying over it. In these cases, it may be difficult to find suitable points of engagement for repositioning forceps. It has hitherto been necessary to screw a bone plate onto a bone fragment in order to create a point of engagement for a repositioning instrument.

When the bone plates are suitably interconnected, they can be used as a lever that facilitates the process of repositioning. In the simplest case, the repositioning and fixation system comprises two elongate bone plates which each have a connector element arranged at the center of the bone plate. A connector element arranged at the center is referred to when the connector element is at a distance from both ends of the bone plate. Connector elements arranged at the periphery form the counterpart. When the two bone plates are interconnected at their center, they form a scissors-type structure. The hinge of the scissors-type structure can be used as a fulcrum. Two ends of the scissors-type structure are for this purpose secured to two bone fragments. The opposite ends of the scissors-type structure can be engaged by forceps in order to move the bone fragments relative to each other. When the scissors structure is spread out with the aid of the forceps, the bone fragments are also spread apart from each other. Soft-tissue parts that have become caught between them can be freed. By closing the scissors structure, the bone fragments can then be brought together such that they come to lie next to each other. In particular, the bone plates can also be used in this way when access to the fracture site is not possible with large repositioning forceps.

Alternatively, the repositioning and fixation system can also comprise four bone plates that each have two connector elements arranged at the periphery. These bone plates can be interconnected in such a way that they together form a square whose arms can be mutually pivoted in the manner of a hinge. When two arms of the square are connected to bone fragments, the two other bone fragments can then be gripped by forceps in order to move the bone fragments relative to each other. This embodiment of the repositioning and fixation system can also be advantageously used if the fracture site is not directly accessible to repositioning forceps. Moreover, this embodiment is suitable when a large number of bone fragments have to be repositioned. This is often the case, for example, in fractures of the hip bone or of the shoulder blade.

In another embodiment, the repositioning and fixation system again comprises four bone plates, but these each have a connector element arranged at the center and a connector element arranged at the periphery of the bone plate. Two bone plates are in each case interconnected at the center to form a scissors-type structure. The two scissor structures are interconnected via the peripheral connector elements to form a slidable lattice structure. If necessary, a plurality of scissors-type structures can be joined up to form a longer slidable lattice. With a repositioning and fixation system in the form of a slidable lattice, it is possible to bridge a greater distance between the fracture site and the point where the forceps are engaged. It is also possible for slidable lattices to be extended in width by attachment of further bone lattices, resulting in a slidable lattice of planar configuration. A planar slidable lattice can be used in particular when bone fragments of a flat bone such as the hip bone or shoulder blade have to be repositioned.

For transmitting force in the longitudinal direction, the slidable lattice structure additionally has the advantage of providing a transmission ratio in which the forceps cover a large distance, whereas the bone fragments connected to the opposite end only move a short distance. This embodiment is therefore particularly suitable when considerable force is needed to reposition the bone fragments. The embodiments in which the repositioning and fixation system is used as a lever or as a point of engagement for forceps also deserve protection independently of the features of claim 1. If necessary, the scissors-type structures and slidable lattice structures can be suitably combined with further bone plates.

BRIEF DESCRIPTION OF THE DRAWINGS

The invention is described below on the basis of an advantageous illustrative embodiment and with reference to the attached drawings, in which.

DESCRIPTION OF THE INVENTION

Figure 1:
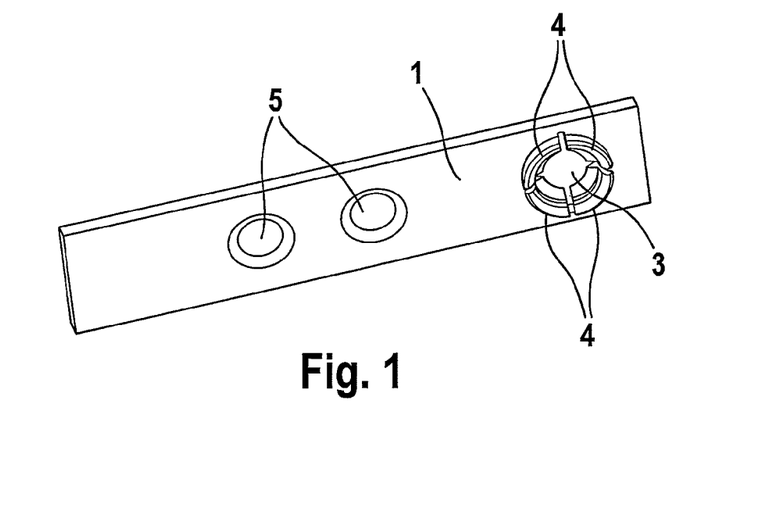
FIG. 1 shows a first bone plate of a repositioning and fixation system according to the invention.
Figure 2:
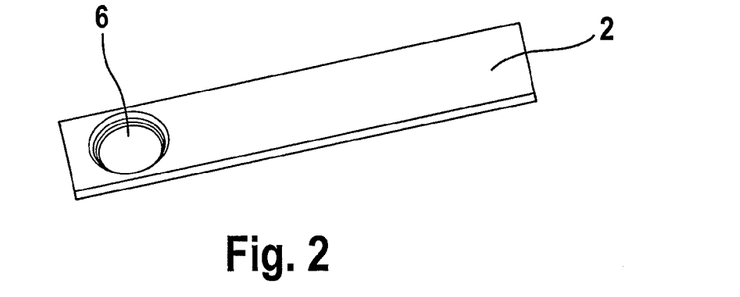
FIG. 2 shows a second bone plate of a repositioning system according to the invention.

The repositioning and fixation system comprises a first bone plate 1 (FIG. 1) and a second bone plate 2 (FIG. 2). The first bone plate 1 has a bore 3, and four projections 4 arranged at the circumference of the bore 3. The projections 4 form a connector element for connection to another bone plate. The bone plate 1 has further bores 5. The second bone plate 2 is provided with an opening 6. The opening 6 forms a connector element for the connection to another bone plate.

The projections 4 comprise a segment 41 close to the bone plate and a segment 42 remote from the bone plate. The segments 42 of the projections 4 remote from the bone plate can be enclosed by an imaginary circle whose diameter is greater than the smallest diameter of the opening 6. The smallest diameter of the opening 6 is formed by a bead 61 in the wall of the opening. The segments 41 of the projections 4 close to the bone plate can be enclosed by an imaginary circle whose diameter corresponds to the smallest diameter of the opening 6.

In the initial state shown in FIGS. 1 and 2, the bone plates 1, 2 are separate from each other. To bring the bone plates to the first connection state, shown in FIG. 3, the projections 4 of the first bone plate 1 are inserted into the opening 6 of the bone plate 2. To allow the segments 42 remote from the bone plate to be inserted into the opening 6, the projections 4 have to be tensioned in an inward direction, such that they can be enclosed by an imaginary circle whose diameter is not greater than the diameter of the bead 61. The projections 4 are tensioned in an inward direction by placing the opening 6 onto the projections 4 and by pressing the first bone plate 1 and the second bone plate 2 together. The bead 61 tensions the projections 4 in an inward direction, slides past the segments 42 of the projections 4 remote from the bone plate, and comes to lie next to the segments 41 of the projections 4 close to the bone plate. The projections 4 spring back into the untensioned initial position.

Figure 3:
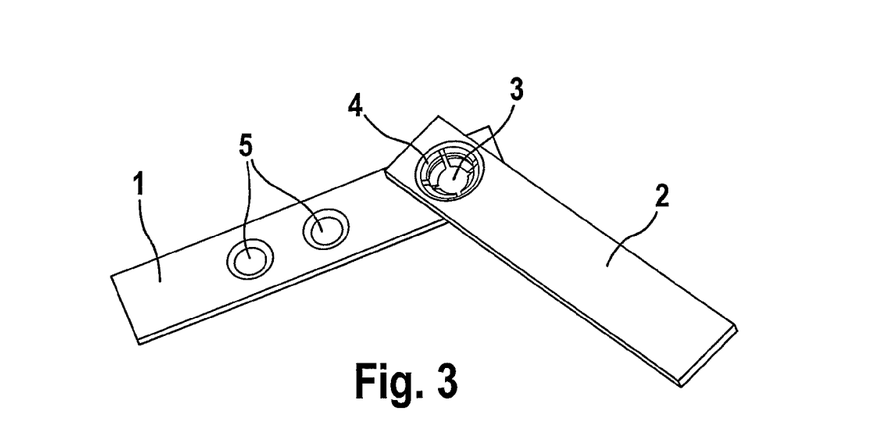
FIG. 3 shows a repositioning and fixation system with the bone plates from FIG. 1 and FIG. 2 in the first connection state.
Figure 4:
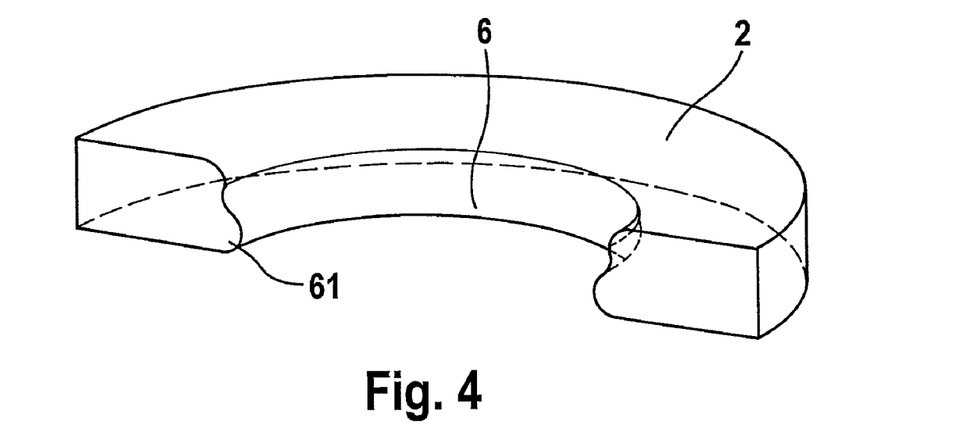
FIG. 4 shows an enlarged detail from FIG. 2.
Figure 5:
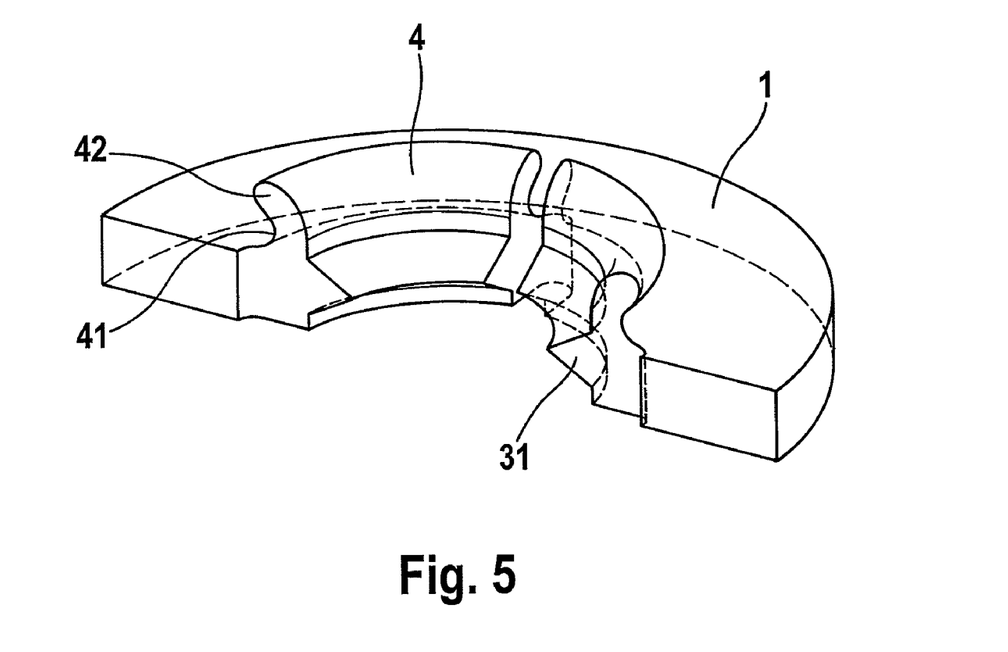
FIG. 5 shows an enlarged detail from FIG. 1.
Figure 6:
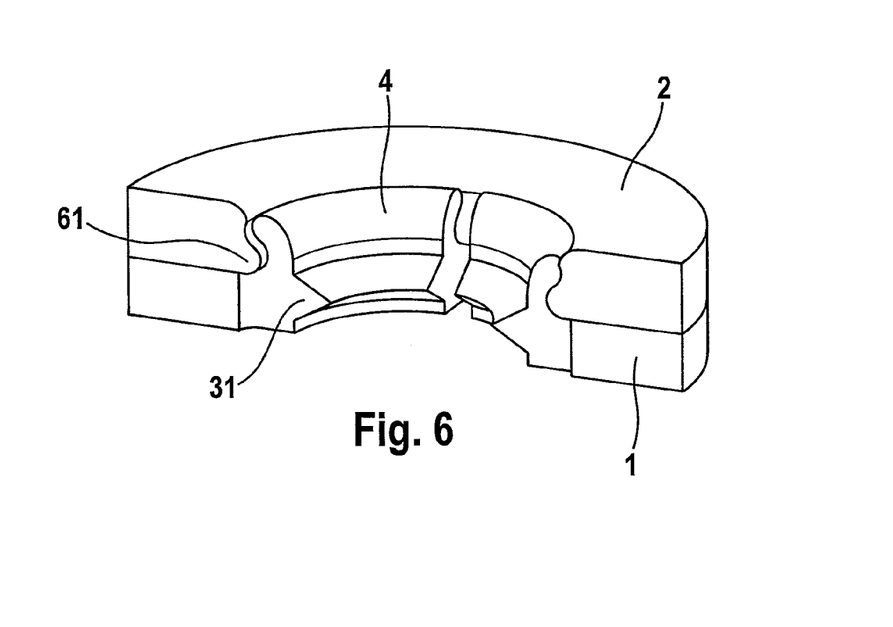
FIG. 6 shows the details from FIG. 4 and FIG. 5 in the first connection state.

The segments 42 of the projections 4 remote from the bone plate engage behind the bead 61 in the opening 6, such that the second bone plate 2 cannot be readily detached again from the first bone plate 1. The only movement that the second bone plate 2 can make relative to the first bone plate 1 is a pivoting movement about the axis of the opening 6. The bearing for this pivoting movement is formed by the bead 61 and by the segments 41 of the projections 4 close to the bone plate.

Figure 7:
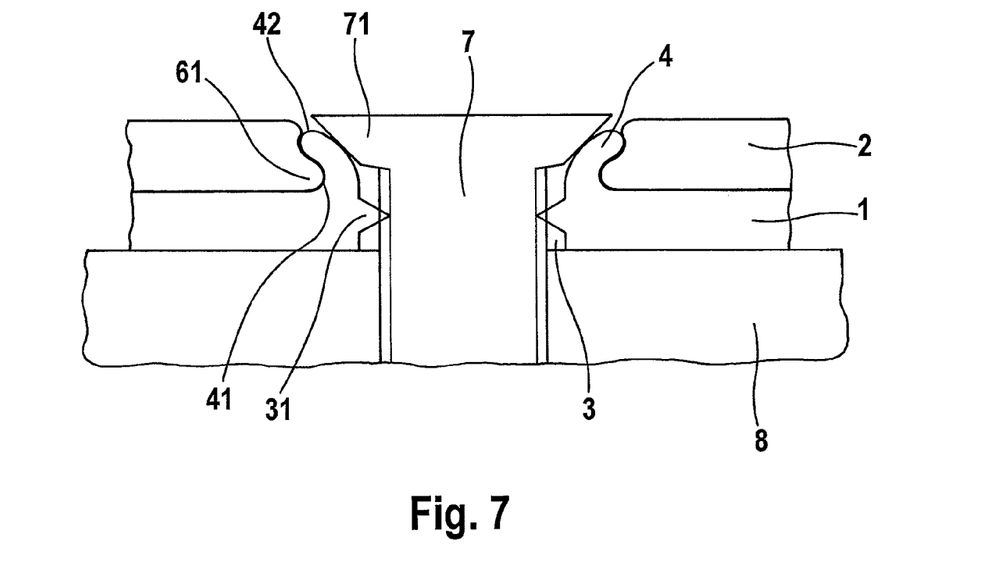
FIG. 7 shows a cross section through a repositioning and fixation system according to the invention in the second connection state.

To bring the bone plates 1, 2 to the second connection state, shown in FIG. 7, a screw 7 is guided through the opening 6 in the first bone plate 1 and through the bore 3 in the second bone plate 2 and is screwed into a bone fragment 8 lying on the first bone plate 1. The tensile force of the screw 7 presses the head 71 of the screw 7 against the projections 4. The projections 4 are spread apart such that the segments 41 of the projections 4 close to the bone plate are pressed against the bead 61. The bearing formed by the bead 61 and the projections 4 is blocked. A pivoting of the first bone plate 1 relative to the second bone plate 2 is no longer possible. At the same time, the pressure exerted by the screw head 71 on the projections 4 has the effect that the ends 42 of the projections 4 remote from the bone plate are bent round and press onto the bead 61 from above. The effect of this force is that the second bone plate 2 is pressed against the first bone plate 1. As FIG. 8 shows, the bone plates 1, 2 have elevations 10 and depressions 11 that extend radially from the opening 6 in the contact area and that further increase the friction between the first bone plate 1 and the second bone plate 2.

The bore 3 has a lip-shaped constriction 31. The diameter of the opening enclosed by the constriction 31 is smaller than the external diameter of the screw 7. As the screw 7 is screwed in, a cold-forming of the lip-shaped constriction 31 takes place. The thread of the screw 7 cuts a thread into the constriction 31, and at the same time the material of the screw connects firmly to the material of the lip-shaped constriction 31. A rigid connection is established between the screw 7 and the first bone plate 1, by which means the second bone plate 2 is also brought into rigid connection to the first bone plate 1.

In surgical correction of bone fractures, the described repositioning and fixation system is initially brought to the first connection state (FIG. 3). By way of the bores 5, the first bone plate 1 is secured to a bone fragment by screws. Normal screws can be used that are guided through the bore 5. However, it is also possible to use screws which, in the course of the cold-forming, interact with the bore 5 and in doing so produce a rigid connection to the bone plate 1. The second bone plate 2 is then secured by suitable means to another bone fragment which at this point does not yet have to be in the correct position relative to the first bone fragment. For this purpose, the second bone plate 2 can likewise have bores, although these are not shown in FIG. 3. By pivoting of the two bone plates 1, 2, the bone fragments are brought to the correct position relative to each other. Once the correct position of the bone fragments has been reached, the projections 4 are tensioned by a screw, such that the two bone plates are in a rigid position relative to each other. The two bone fragments are fixed in their position.

Figure 8:
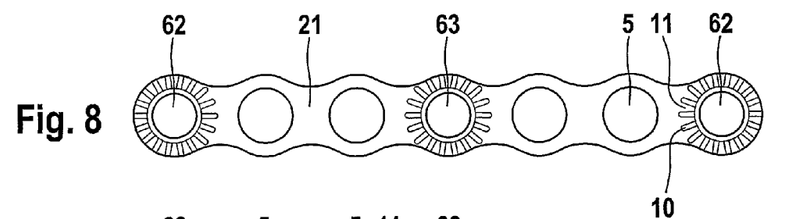
FIG. 8 shows a plan view of an embodiment of a bone plate according to the invention.
Figure 9:
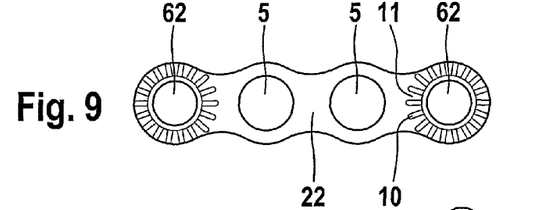
FIG. 9 shows a plan view of another embodiment of a bone plate according to the invention.

Other embodiments of the second bone plate are shown in FIGS. 8 and 9. The bone plate 21 in FIG. 8 has three openings 62, 63 designed as connector elements, and four bores 5 arranged between the openings 62, 63. The opening 63 is arranged at the center of the bone plate 21, while the openings 62 are arranged at the periphery of the bone plate 21. A further bone plate can be connected to each of the openings 62, 63. Screws can be guided through the bores 5 and screwed into bone fragments. The bone plate 22 in FIG. 9 has two openings 62 designed as connector elements, and two bores 5 lying between these. Bone plates designed analogously to the bone plates 21, 22, but having projections 4 instead of the openings 62, 63, are not shown.

Figure 10:
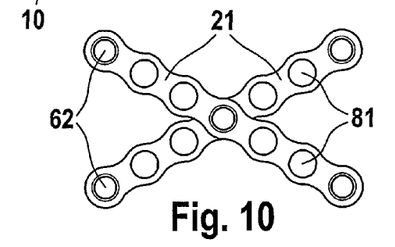
FIG. 10 shows a repositioning and fixation system composed of two bone plates according to FIG. 8.

The bone plates 21, 22 can be combined with each other in various ways. A few combinations are shown in FIGS. 10 to 14. In FIG. 10, two bone plates 21 are interconnected like scissors via the central opening 63. When the bone plates 21 are connected to bone fragments via the bores 81, the opposite ends of the scissors-type structure can be gripped by forceps in order to reposition the bone fragments.

Figures 11, 12:
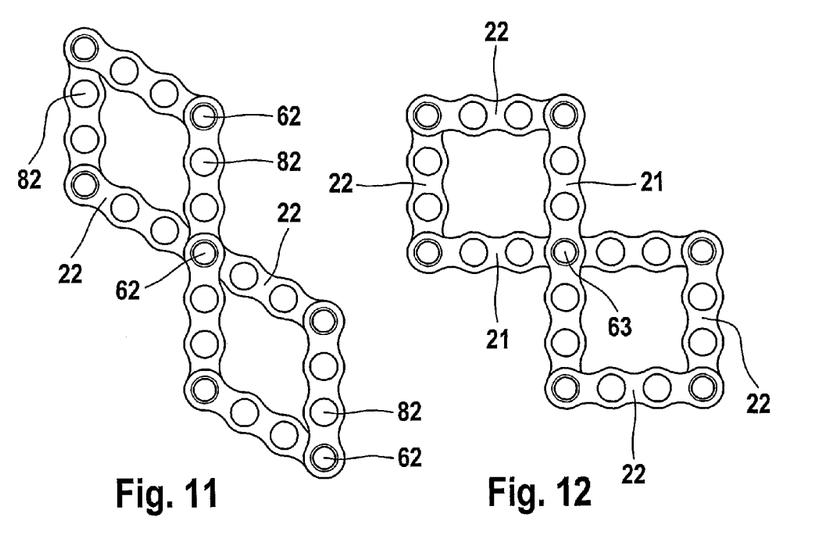
FIG. 11 shows a repositioning system composed of eight bone plates according to FIG. 9.
FIG. 12 shows a repositioning and fixation system composed of two bone plates according to FIG. 8 and four bone plates according to FIG. 9.

In FIG. 11, eight bone plates 22 are interconnected via the peripheral openings 62. All the bone plates 22 can be pivoted relative to one another. It is possible, for example, for three bone fragments to be securely screwed via the bores 82 and repositioned by suitable pivoting of the bone plates 22. This embodiment is suitable in particular for flat bones such as the hip bone and the shoulder blade, where a plurality of bone fragments can be repositioned.

The embodiment in FIG. 12 is based on the scissors-type structure shown in FIG. 10. The scissors-type structure is supplemented by four bone plates 22. In contrast to the embodiment in FIG. 11, there are fewer degrees of freedom here during pivoting of the bone plates, but the bone plates 21 can be used as levers for the transmission of forces.

Figure 13:
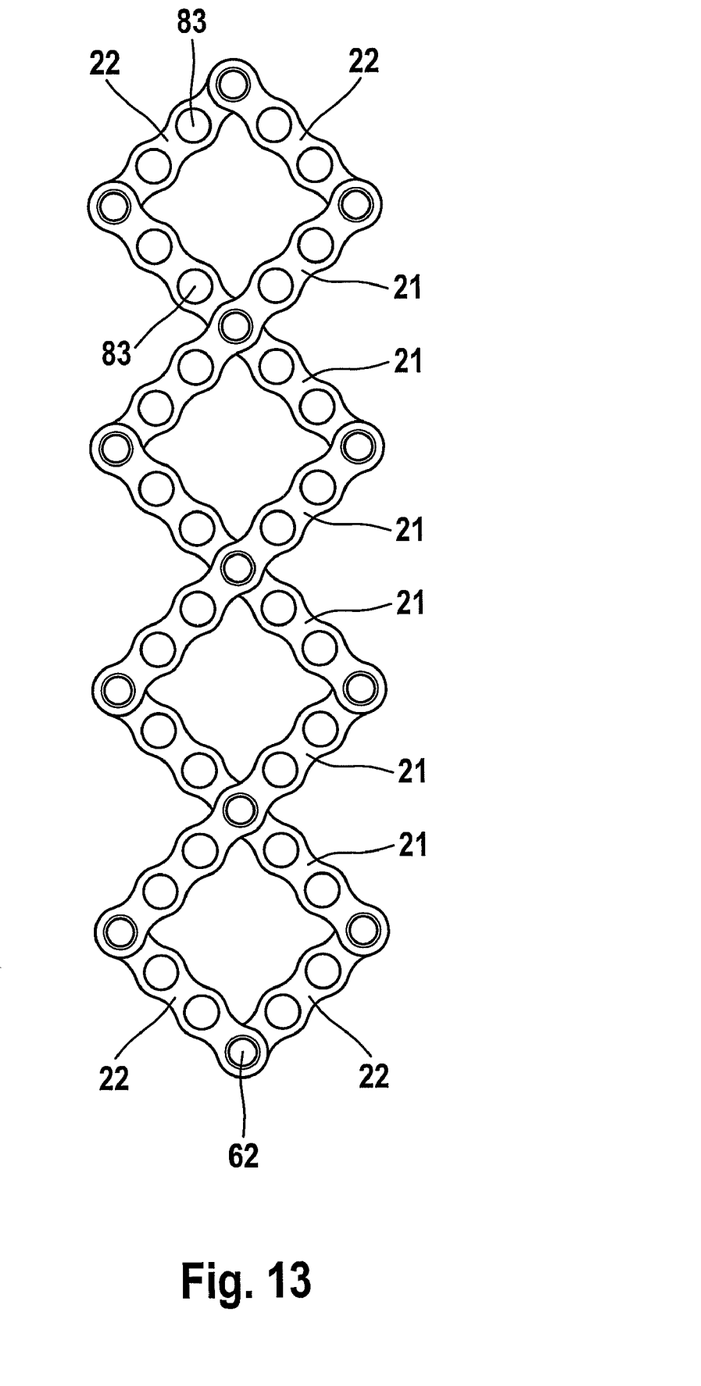
FIG. 13 shows a repositioning and fixation system composed of six bone plates according to FIG. 8 and four bone plates according to FIG. 9.
Figure 14:
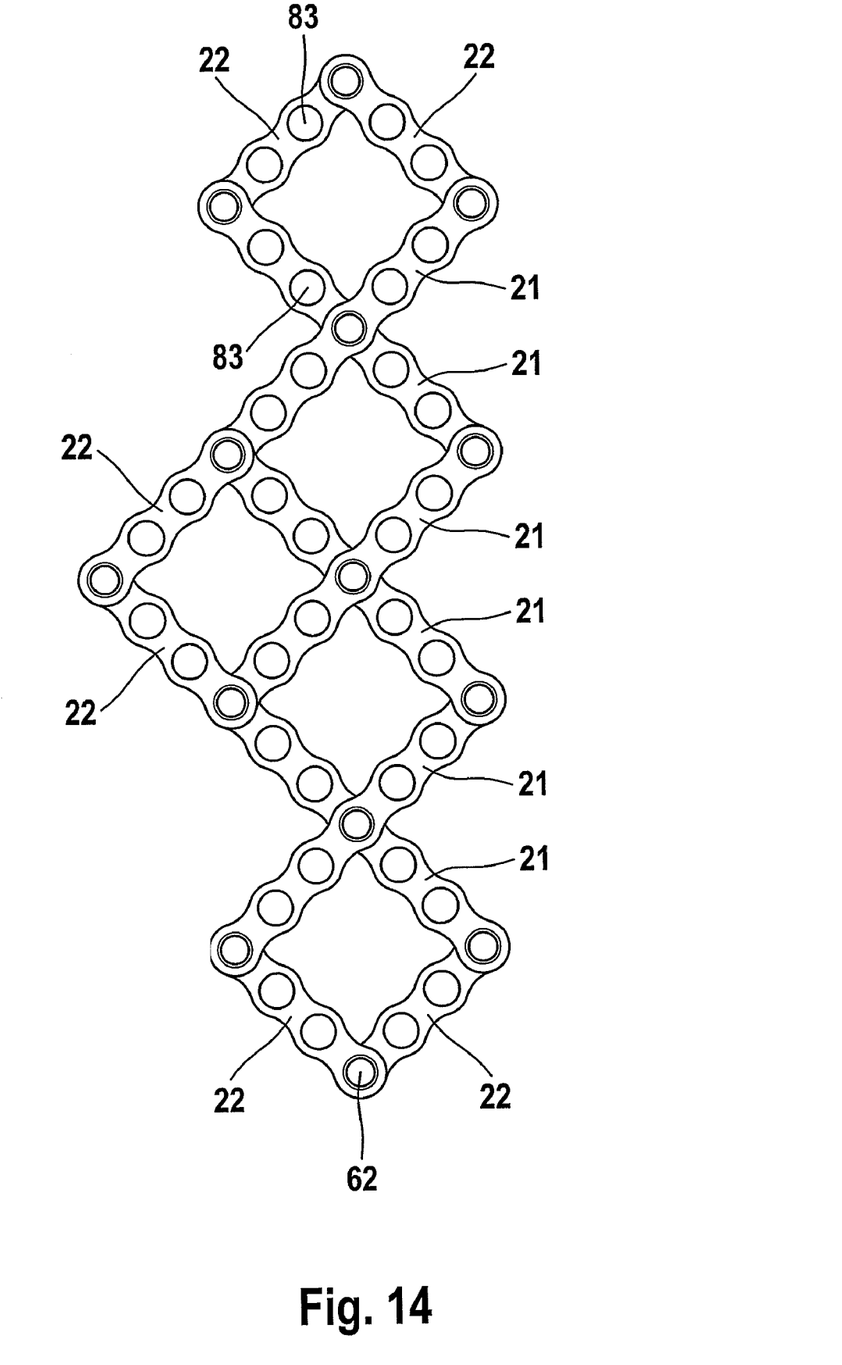
FIG. 14 shows the repositioning and fixation system from FIG. 13 with two further bone plates.

In the repositioning and fixation system in FIG. 13, six bone plates 21 are connected to two bone plates 22 to form a slidable lattice structure. The slidable lattice provides a transmission ratio for transmitting lengthwise forces. If two bone fragments are connected to the bores 83, for example, and if the opposite end of the slidable lattice is pulled by forceps, the tensile force acting on the bone fragments is substantially greater than the force exerted by the forceps. In FIG. 14, the slidable lattice from FIG. 13 is supplemented by a further two bone plates 22.

The invention claimed is:

1. A repositioning and fixation system for bone fragments, comprising at least two interconnectable bone plates, each bone plate comprising a connector element for connection to another bone plate, and a screw, wherein:

the connector element of a first bone plate of the at least two interconnectable bone plates comprises a plurality of projections;

the connector element of a second bone plate of the at least two interconnectable bone plates comprises an opening;

the first bone plate comprises a bore and the projections are arranged at the circumference of the bore;

the projections are configured to engage in the opening and produce a hinge-type connection between the first bone plate and the second bone plate in a first connection state;

the projections are configured to be tensioned to produce a rigid connection between the first bone plate and the second bone plate in a second connection state; and the screw, in the second connection state, can be guided through the opening in the second bone plate and through the bore in the first bone plate such that the head of the screw subjects the projections to tensioning.

2. The repositioning and fixation system of claim 1, wherein the screw, in the second connection state, is configured to be in rigid connection to the first bone plate and to the second bone plate.

3. The repositioning and fixation system of claim 2, wherein the rigid connection is based on a cold-forming that occurs as the screw is screwed in.

4. The repositioning and fixation system of claim 1, wherein the projections comprise segments remote from the bone plate, the segments are connectable, in an untensioned state, to an imaginary circle, and the diameter of the imaginary circle is greater than the diameter of the opening of the second bone plate.

5. The repositioning and fixation system of claim 1, wherein the projections comprise segments close to the bone plate, the segments are connectable, in an untensioned state, to an imaginary circle, and the diameter of the imaginary circle corresponds to the diameter of the opening of the second bone plate.

6. The repositioning and fixation system of claim 1, wherein the first bone plate and the second bone plate, in the second connection state, lie flat on each other in a contact area, and at least one of the bone plates has elevations and depressions in the contact area.

7. The repositioning and fixation system of claim 6, wherein the elevations and depressions are oriented radially with respect to at least one of the bore in the first bone plate and the opening in the second bone plate.

8. The repositioning and fixation system of claim 1, wherein each bone plate comprises more than one connector element.

9. The repositioning and fixation system of claim 1, wherein each bone plate has an elongate shape.

10. The repositioning and fixation system of claim 9, wherein the bone plates have a connector element arranged at the center of the bone plate.

11. The repositioning and fixation system of claim 9, wherein the system comprises four bone plates, and each bone plate comprises a connector element arranged at each end of the bone plate.

12. The repositioning and fixation system of claim 9, wherein the system comprises four bone plates, and each bone plate comprises a connector element arranged at the center of the bone plate and a connector element arranged at an end of the bone plate.

\* \* \* \* \*

UNITED STATES PATENT AND TRADEMARK OFFICE
CERTIFICATE OF CORRECTION

PATENT NO. : 8,287,542 B2  
APPLICATION NO. : 12/520813  
DATED : October 16, 2012  
INVENTOR(S) : Dietmar Wolter Page 1 of 1

It is certified that error appears in the above-identified patent and that said Letters Patent is hereby corrected as shown below:

Title page, item [76] under Inventor, replace "Holsdorf" with --Hoisdorf--.

Signed and Sealed this
Twelfth Day of February, 2013

Teresa Stanek Rea
*Acting Director of the United States Patent and Trademark Office*